US00PP09378P

United States Patent [19]

Tooby

[11] Patent Number: Plant 9,378

[45] Date of Patent: Nov. 21, 1995

[54] HEBE 'ROSIE'

[75] Inventor: Hubert J. Tooby, Worchester, Great Britain

[73] Assignee: John Tooby & Co. Ltd., Worcester, United Kingdom

[21] Appl. No.: 337,527

[22] Filed: Nov. 8, 1994

[51] Int. Cl.[6] ..... A01H 5/00

[52] U.S. Cl. ..... Plt./67.2

[58] Field of Search ..... Plt./67.2

*Primary Examiner*—James R. Feyrer

*Attorney, Agent, or Firm*—Young & Thompson

[57] ABSTRACT

A new and distinct and highly precocious hebe, or veronica plant, attained from 'Great Orme'×'Mourning Clouds', which is particularly distinguised by its compact, dense canopy, small size, and its prolific production of bright pink flowers on racemes flushing intermittently for about four months, or more, beginning from about mid June.

1 Drawing Sheet

HISTORY

The present invention relates to a new variety of Hebe called 'Rosie' which the inventor has produced in the course of his studies and research aimed at finding new products capable of increasing the profits of horticulturists by virtue of their superior performance in gardens.

The new variety which is the subject of the present invention occurred as a selection from about 2,000 seedlings which arose in 1982, mainly from seed of Hebe 'Great Orme' with cross-pollination coming mainly from Hebes 'Morning Clouds' and 'James Platt' which were growing nearby.

The new variety which is the subject of the present invention is different from all other Hebes known heretofore and constitutes with respect to the latter an improvement, namely the combination of a bright pink color, a dwarf growth and a very free-flowering habit. It has inherited the pink flower form 'Great Orme' and its dwarf growth from 'Morning Clouds' or 'James Platt'. It is much more free-flowering than either and hardier than 'Great Orme' and is therefore a much more desirable garden plant.

Its performance is enhanced by trimming it all over in the spring which stimulates many more terminals and therefore many more racemes of flowers, as depicted in the accompanying photographic illustrations.

The new variety which is the subject of the present invention has been propagated by cuttings by the applicant nursery at their premises at Bransford and in other parts of England and over 500,000 plants have been raised and all clones appear absolutely identical to the original plant.

The identification of the colors in the Description was made in accordance with the tables of the ROYAL HORTICULTURAL SOCIETY COLOUR CHART of London (indicated in the text by the initials RHS followed by the number of the table which most nearly matches the color of the part of the plant concerned).

BRIEF DESCRIPTION OF THE VIEWS OF THE DRAWINGS

The new Hebe plant 'Rosie' of this invention is depicted in the color photographs of the drawings in which:

The first photograph depicts a market-stage specimen of the plant in a container for transplanting in perspective, at optimum stage for marketing and transplanting; and shows the plant's symmetrical mounded figure, the moderate to high density of the canopy formed, the leaf and branching habit of the plant at the mid to late portion of the first season after starting from a cutting and judicious trimming having been employed.

And, the second color photograph illustrates at closer range in side view the flowering of the Hebe plant 'Rosie' showing the color and form of the delicate flowers of the raceme, the characteristics, color and high number of early and late stage unopened buds, and the color of the new growth and the stem terminal of a mature specimen of this plant during the initial flush of flowers of the season.

The colors depicted in the drawings are shown as nearly accurate as is reasonably possible in photographic reproductions of this type.

DETAILED BOTANICAL DESCRIPTION OF THE PLANT

Origin: Chance seedlling: one parent 'Great Orme', the other probably 'Morning Clouds' or 'James Platt'.

Plant:

- *Habit.*—Rounded to spreading; naturally rather open quite dense when trimmed.
- *Size.*—Attains about 12 inches in the first year after planting; an untrimmed plant in the originator's garden is 2–2½ feet high and 3–4 feet across at 9 years after planting.
- *Density.*—Medium if untrimmed; quite dense when trimmed.
- *Vigor.*—Annual growth is about 4–6 inches in a growing season.
- *Young shoots.*—Finely pubescent.
- *Color of stems.*—RHS 144B when young; RHS 156B when mature.
- *Internodes.*—Short; about a quarter of an inch when young to htree quarters of an inch when mature.

Leaves:

- *Shape.*—Simple, oblong, entire, with obtuse apex and cuneate base.
- *Size.*—One third to three quarters of an inch long by one sixth to one quarter of an inch wide.
- *Young leaves.*—Color RHS 148A, touched and shaded RHS 177B and RHS 178A.
- *Mature leaves.*—Color RHS 137B on upper side and near 148B on lower side.

Inflorescence: Many, in pairs of racemes (ocassionally single racemes), arising form successive nodes, giving a compound appearance; 3–5 pairs per terminal on young plants; 2–4 pairs per terminal on older plants.

*Racemes.*—Each about 2 inches in length, carrying about 20 flowers.

*Peduncles.*—About about three quarters of an inch long.

*Peduncles.*—About one twelfth of an inch long.

Flower:

*Depth.*—About four tenths of an inch.

*Diameter.*—About one third of an inch.

*Gender.*—Hermaphrodite; not different from Hebes generally.

*Calyx lobes.*—Narrow ovate; about one twelfth of an inch long.

*Corolla color.*—Near RHS 58C on lower surface; near RHS 56A on upper surface; fading paler with age especially in hot climates.

*Flowering season.*—Late June to first frost.

ADDITIONAL INFORMATION

Resistance to pests and diseases: As with other dwarf Hebes.

Hardiness: Hardy to about 10 degrees Fahrenheit.

Flowers/young leaves likely to be damaged by frost: No.

Special soil conditions required: Will thrive in any soil, provided it is not poorly drained.

Growing conditions: The flower color is paler in hot climates.

Can distinguishg characteristics of variety be seen in young plants: Yes.

Propagation: Because of its highly floriferous nature certain precautions need to be taken in propagating and growing on young plants: avoid conditions of high humidity; avoid wetting the leaves for long periods of time; avoid cutting back young plants too severely, especially outdside the sprig period.

I claim:

1. The new and distinct variety of Hebe as described and illustrated.

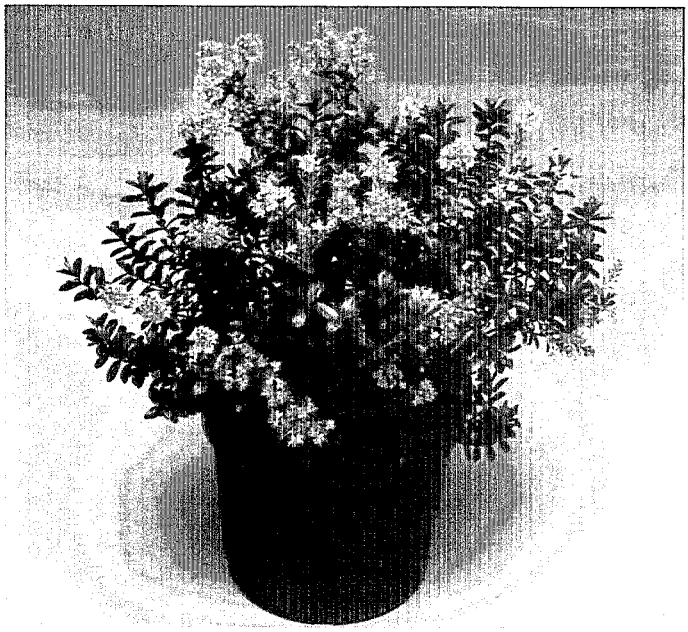
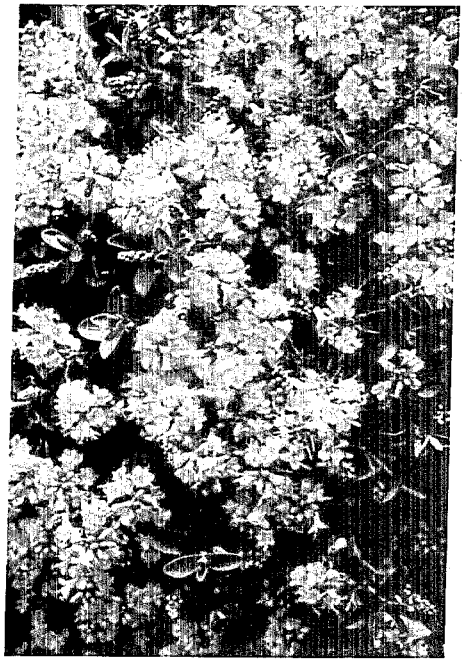

* * * * *